United States Patent
Petrich et al.

(10) Patent No.: US 6,758,618 B2
(45) Date of Patent: Jul. 6, 2004

(54) CONTAINER AND APPLICATOR ASSEMBLY

(75) Inventors: Robert W. Petrich, Woodbury, MN (US); Larry D. Fleisher, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/322,906

(22) Filed: Dec. 19, 2002

(65) Prior Publication Data

US 2003/0093026 A1 May 15, 2003

Related U.S. Application Data

(62) Division of application No. 09/838,883, filed on Apr. 20, 2001, now Pat. No. 6,592,280.

(51) Int. Cl.[7] ............................................... A45D 33/00
(52) U.S. Cl. ....................... 401/130; 401/126; 401/122; 401/121; 433/215
(58) Field of Search ................................ 401/126, 127, 401/129, 128, 118, 121, 122, 132; 433/216, 215

(56) References Cited

U.S. PATENT DOCUMENTS

| | | | |
|---|---|---|---|
| 3,121,906 A | | 2/1964 | Hulsh |
| 3,613,697 A | | 10/1971 | Andrews |
| 3,951,157 A | * | 4/1976 | Idec ........................... 401/122 |
| 4,805,646 A | | 2/1989 | Shimenkov |
| 4,828,419 A | | 5/1989 | Porter et al. |
| 4,878,589 A | * | 11/1989 | Webster et al. ............. 215/252 |
| 4,889,228 A | | 12/1989 | Gueret |
| 4,952,204 A | | 8/1990 | Korteweg |
| 4,997,500 A | | 3/1991 | Arnett et al. |
| 5,001,803 A | | 3/1991 | Discko, Jr. |
| 5,006,004 A | | 4/1991 | Dirksing et al. |
| 5,150,495 A | | 9/1992 | Discko, Jr. et al. |
| 5,163,441 A | | 11/1992 | Monthony et al. |
| 5,226,744 A | * | 7/1993 | Kemmerer ..................... 401/4 |
| 5,511,654 A | | 4/1996 | de la Rocha |
| 5,514,120 A | | 5/1996 | Johnston et al. |
| 5,660,273 A | | 8/1997 | Discko, Jr. |
| 5,794,632 A | | 8/1998 | Gueret |
| 5,829,976 A | | 11/1998 | Green |
| 5,874,045 A | | 2/1999 | Chisum |
| 5,938,438 A | | 8/1999 | Chipman et al. |
| 5,989,229 A | | 11/1999 | Chiappetta |
| 6,227,737 B1 | | 5/2001 | Lightfoot |
| 6,287,034 B1 | * | 9/2001 | Miraglia et al. ............ 401/122 |

FOREIGN PATENT DOCUMENTS

| | | |
|---|---|---|
| DE | 196 00 118 | 7/1997 |
| EP | 0 411 578 | 2/1991 |
| EP | 0 357 261 | 1/1995 |
| FR | 1207758 | 2/1960 |
| FR | 1320865 | 2/1963 |
| WO | WO 99/65704 | 12/1999 |

OTHER PUBLICATIONS

Microbrush, "Dispenser Series Disposable Applicator", 1 page.
Microbrush & Ultrabrush, "Dispenser Series Instructions for Assembly", 1 page.
Microbrush, ProTouch, Disposable Touch–Up Microbrush.
Pending U.S. patent application Ser. No. 09/838,875 filed Apr. 20, 2001.
Pending U.S. patent application Ser. No. 09/512,509 filed Feb. 23, 2000.

* cited by examiner

Primary Examiner—David J. Walczak
(74) Attorney, Agent, or Firm—James D. Christoff

(57) ABSTRACT

A container and applicator assembly includes an applicator with a handle and a dispensing tip, and a container with a chamber that detachably receives at least part of the applicator. The container has an inner surface with a plurality of protrusions that extend in the chamber along side portions of the tip. The protrusions facilitate distribution of the composition across the tip and also help to prevent unintentional movement of the composition to other areas.

17 Claims, 3 Drawing Sheets

CONTAINER AND APPLICATOR ASSEMBLY

RELATED APPLICATION DATA

This application is a divisional of application Ser. No. 09/838,883, filed Apr. 20, 2001, now U.S. Pat. No. 6,592,280.

BACKGROUND OF THE INVENTION

1. Field of the Invention

This invention relates to a packaged assembly that includes a container and an applicator for applying a composition to a work site. The invention also relates to a method of dispensing a composition.

2. Description of the Related Art

Applicators for applying compositions to surfaces are in widespread use in a variety of medical, commercial and household applications. Typical examples of such applicators include brushes and swabs having an overall stick-like configuration. Applicators that are relatively inexpensive represent a significant convenience to the user, in that the applicator can be disposed of after a single use.

In some instances, disposable applicators are individually packaged in closed, sealed containers. Individually packaged applicators are an advantage in medical and dental operatories because sterility of the applicator can be assured until such time as the applicator is removed from the package in preparation for use. Examples of known packaged applicators include swabs that are contained between two sheets of a plastic or paper film, and swabs that are contained within a plastic tube or casing.

Another type of disposable applicator that is known in the art has been available from Microbrush Corporation of Orlando, Fla. under the name "Microbrush". This applicator has an elongated handle that is connected to an outer tip. The tip is flocked with a number of small fibers that facilitate spreading of a composition over the application site. The handle includes a reduced-diameter flexible portion that can be bent past its yield point to a desired angular orientation to facilitate placement of the composition in certain instances, such as when it is necessary to apply the composition to an area where access is limited.

In some procedures, the composition to be applied by the applicator is provided in bulk containers. In those instances, the users may elect to dip the swab or brush tip of the applicator directly into the container in order to coat the tip with a small quantity of the composition. The tip is then removed from the container and moved across the desired surface in order to transfer the composition from the tip to the surface.

However, the practice of dipping the applicator tip directly into a bulk container is not satisfactory in many medical and dental applications due to the possibility of cross-contamination between patients. For example, if the applicator is used in a dental procedure to apply an adhesive to the surface of tooth structure, the practitioner may unknowingly transfer infectious disease from one patient to another if the applicator is returned to the bulk container after initial use in the oral cavity. The issue of cross-contamination can be avoided by using a new applicator in those instances where additional composition is needed, but such practice represents an additional expense and also requires a certain amount of time for retrieving, opening and preparing a new packaged applicator for use.

The problems of cross-contamination as mentioned above can be avoided by use of a dispensing well or pad. For example, in dental procedures a small quantity of composition is dispensed from the bulk container onto the well or pad, and the tip of the applicator is then used to transfer the composition from the well or pad to the patient's tooth structure. Such practice avoids the need for returning the applicator to the bulk container so that issues of cross-contamination between patients can be avoided. Once the procedure has been completed, the well or pad is disposed of or cleaned for reuse.

In recent years, there has been increased interest in packaged, disposable applicators having a tip that is pre-supplied with a quantity of a composition. These prepackaged applicators are a significant advantage in that the time that would otherwise be associated with handling of a bulk container and a dispensing well or pad can be avoided. Moreover, such packaged applicators are a particular advantage when used with compositions that are messy or that are considered hazardous.

One example of a packaged swab assembly is described in U.S. Pat. No. 4,952,204 and includes a swab having a cotton bud that is pre-supplied with a quantity of composition. The swab is contained within a plastic sleeve that includes a relatively small diameter cylindrical handle portion at one end, a substantially larger diameter receptacle portion at the opposite end and a transition portion of compound configuration between the small diameter portion and the larger diameter portion. This patent indicates that when the sleeve is squeezed at the intersection between its larger diameter receptacle portion and its transition portion, the material of the sleeve will snap, crack or tear such that the swab is exposed for use upon removal of the receptacle portion.

Applicant's pending application entitled "PACKAGED APPLICATOR ASSEMBLY", U.S. Ser. No. 09/512,509 filed Feb. 23, 2000 describes an assembly that includes an applicator and a cap, and the applicator includes a flexible portion. As the cap is detached from the applicator, the flexible portion is bent in an arc in order to facilitate use of the applicator, particularly in areas where access is limited. In certain embodiments of the invention described in that application, the cap has an overall, generally cylindrical configuration and provides a reservoir for composition to be dispensed and applied by the tip of the applicator. Optionally, the reservoir includes a compressible porous material such as a synthetic sponge that facilitates retention of the composition in the cap.

While the inventions described in the patent application mentioned above represent a significant advance in the art, there is a continuing need for improvements in this subject area so that manufacture and use of applicators and containers are enhanced. Preferably, such improvements would facilitate handling of the applicator and dispensing of the composition without significantly increasing the overall cost of the assembly.

SUMMARY OF THE INVENTION

The present invention relates to an applicator and container assembly that facilitates handling of a composition to be dispensed. The container includes a roughened surface with a plurality of protrusions that tend to improve distribution of the composition across a tip of the applicator in a uniform manner. As a consequence, subsequent transfer of the composition from the tip to an application site is enhanced.

In more detail, the present invention in one embodiment is directed toward an applicator assembly that comprises an applicator including a handle and a dispensing tip. The tip has side portions and an outer end. The assembly also includes a container that detachably receives at least part of the applicator. The container has an inner surface extending along side portions of the tip, and the inner surface has a plurality of protrusions.

Another embodiment of the invention is directed toward a method of dispensing a composition. The method comprises the act of providing an assembly that includes a container and an applicator, wherein the container has a wall portion with a plurality of protrusions. The method also includes the act of applying a composition to the protrusions, and the act of moving a tip of the applicator across the protrusions while contacting the composition on the protrusions. The method further includes the act of withdrawing the tip from the container.

The surface with protrusions tends to retain the composition. As a result, the composition is less likely to flow from the container when the container is inverted. Moreover, the protrusions facilitate re-wetting of the tip with an additional quantity of the composition when desired.

These and other aspects of the invention are described in more detail below and are illustrated in the accompanying drawings.

DETAILED DESCRIPTION OF THE PREFERRED EMBODIMENTS

Figure 1:
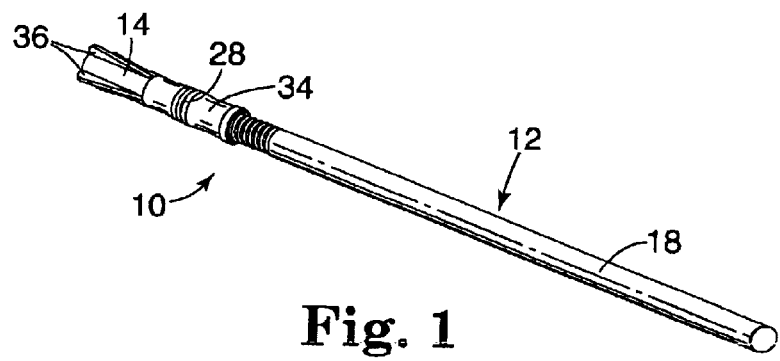
FIG. 1 is a perspective view of an applicator assembly that is constructed in accordance with one embodiment of the present invention.

A container and applicator assembly that is constructed in accordance with one embodiment of the invention is broadly designated by the numeral 10 in FIGS. 1–4. In brief, the assembly 10 includes an applicator 12 and a container 14. The container 14 includes an inner cavity or chamber 16 that initially receives a forward end of the applicator 12.

Figure 2:
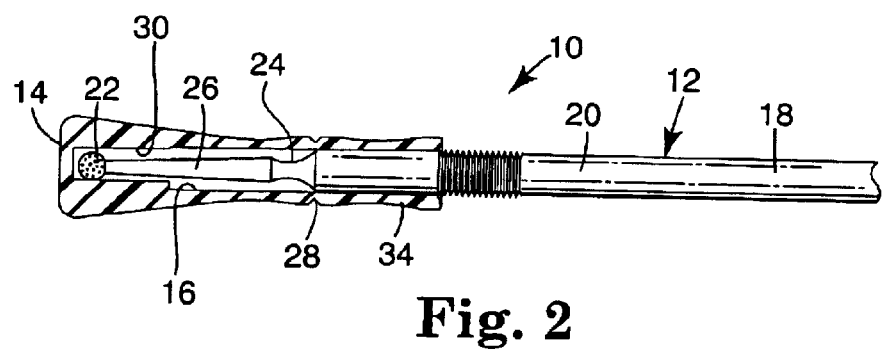
FIG. 2 is a side cross-sectional view of the applicator assembly illustrated in FIG. 1.
Figure 3:
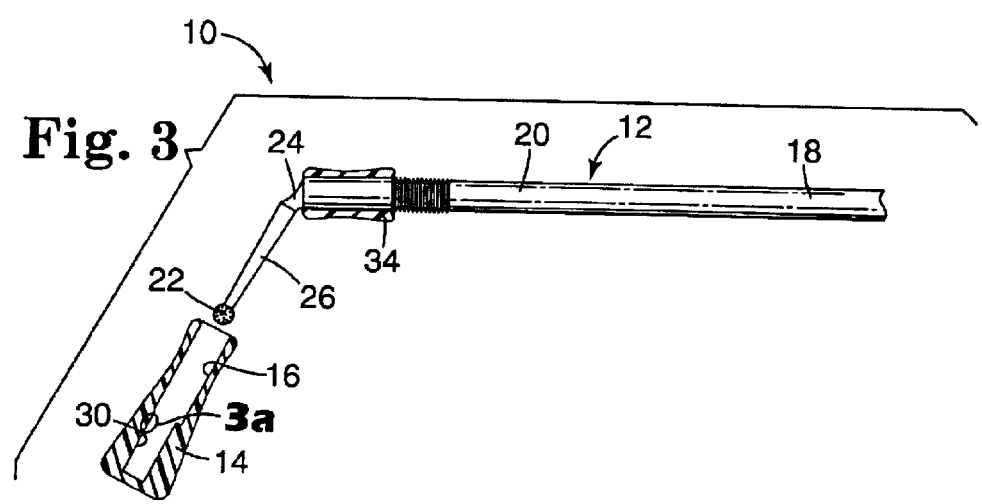
FIG. 3 is a side cross-sectional view of the applicator assembly illustrated in FIGS. 1 and 2 after a container of the assembly has been detached from an applicator of the assembly.

The applicator 12 has an outer handle 18 and an elongated shaft 20 (FIGS. 2 and 3) that is integrally connected to the handle 18. The shaft 20 also includes a tip 22 that is located remote from the handle 18. Optionally, and as illustrated in FIGS. 2 and 3, the tip 22 has a generally spherical configuration, although other shapes are also possible.

Preferably, but not necessarily, the tip 22 has a roughened surface that facilitates spreading of a composition across the surface to which the composition is to be applied. The roughened surface may comprise a material that is made of any suitable structure that is compatible with the composition and functions to distribute the composition over the receiving surface. Suitable materials include small bristles or fibers that serve as a brush and that are applied to all or only part of the tip 22.

Optionally, the fibers can be applied to the tip 22 by a flocking process. The flocking can be carried out by any technique known in the art. Preferably, the flocked fibers define small interstitial spaces that can advantageously fill with the composition, and retain and suspend a small amount of composition for effective application to the surface of interest. The fibers preferably also allow relatively uniform application of the composition over the surface regardless of whether the surface is irregular, rough or smooth, and apply the composition in the same way as a brush would. If used in a dental procedure, the outwardly extending fibers permit the composition to be applied easily to side and overhanging surface of a tooth cavity as well as to the bottom of the tooth cavity.

Alternatively, other types of materials may be applied to the tip 22 for facilitating spreading of the composition across the surface. Examples of such other materials include an open cell foam material such as polyurethane foam or synthetic sponge. Additional examples of suitable materials includes woven and non-woven fabrics from gauzes and the like. Microstructured surfaces could also be employed, including microstructured surfaces that are integrally formed as part of the tip 22.

The shaft 20 of the applicator 12 also includes a flexible portion 24 that is located between the tip 22 and the handle 18. The flexible portion 24 is deformable by finger pressure past its yield point to any one of a number of angular orientations. Once the flexible portion 24 is bent, it will substantially self-remain in a bent orientation without returning to its initially straight orientation. Although some amount of return to its initially straight position is possible, particularly if the flexible portion 24 is made of a resilient material, it is preferred that the flexible portion 24 remain in approximately the same angular orientation to which it is bent after the bending pressure is released.

One method of making a flexible portion 24 includes the provision of one or more grooves that serve to facilitate bending of the shaft 20. In the examples shown in the drawings, the flexible portion 24 includes a single groove that circumscribes the shaft 20. The groove lies in a reference plane that is oriented perpendicular to the longitudinal axis of the shaft 20 and of the assembly 10. However, other constructions are also possible, including the use of a series of grooves, a section of reduced cross-sectional area of another shape or an articulated joint to facilitate bending.

In the embodiment shown in the drawings, the shaft 20 has a tapered portion 26 that is located between the flexible portion 24 and the tip 22. The tapered portion 26 has a generally frustoconical configuration, and advantageously provides clearance in areas adjacent the tip 22 when used in certain applications. For example, if the tip 22 is used to apply a dental composition to overhanging tooth surfaces, the tapered portion 26 facilitates application of the composition in areas beneath that overhanging surface. Examples of dental compositions include a dental primer, a dental adhesive, a dental etchant and a dental sealant.

The chamber 16 of the container 14 surrounds the tip 22, the flexible portion 24 and the tapered portion 26 when the container 14 is connected to the applicator 12. The container 14 is connected to the applicator 12 by any suitable detachable connection known in the art. An example of a suitable detachable connection is a line of weakness 28 (FIGS. 1 and 2) that circumscribes the assembly 10 in a region adjacent the flexible portion 24.

Preferably, the line of weakness 28 is a frangible area of reduced cross-sectional thickness that initially couples the container 14 to the applicator 12. For example, the line of weakness 28 may be a groove that circumscribes the assembly 10 in a reference plane that is perpendicular to the longitudinal axis of the assembly 10. However, other detachable connections are also possible, including the use of an adhesive, a threaded coupling, a friction fit or a pressure sensitive tape that initially retains the container 14 in secure connection to the applicator 12.

The chamber 16 includes a first, generally cylindrical section that extends forwardly from the line of weakness 28 along the tapered portion 26, and a second section that extends from the first section to a forward end of the container, along a forward part of the tapered portion 26 as well as along the tip 22.

An inner, roughened surface 30 having a plurality of protrusions faces the second section of the chamber 16. Preferably, but not necessarily, the roughened inner surface 30 is part of a wall portion that extends along the entire length of the second chamber section. The front inner wall of the container 14 that defines the front end of the second chamber section is optionally smooth.

Figure 4:
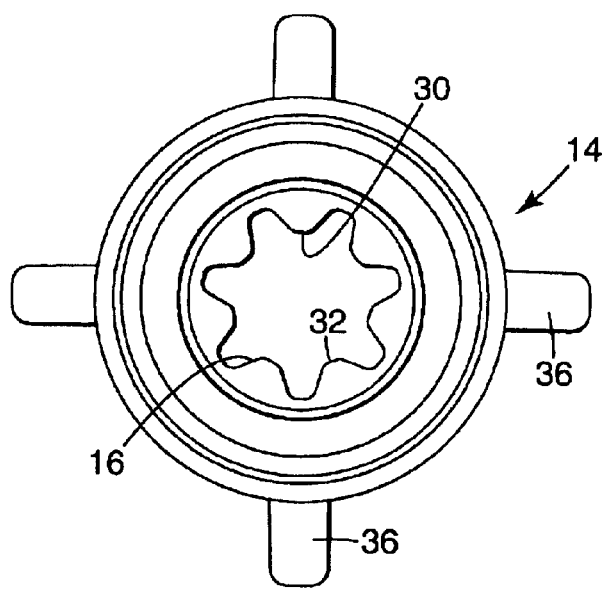
FIG. 4 is an enlarged end view of the container alone that is shown in FIGS. 1–3, looking toward a rear end of the container.

The protrusions of the inner surface 30 may be of any suitable geometry that serves to facilitate retention of a composition in the chamber 16 and enhance wetting of the tip 22 with the composition when desired. An example of a suitable geometry of the inner surface 30 is shown in the enlarged end view of FIG. 4. In FIG. 4, the protrusions comprises a series of ribs 32 that are arranged in a symmetrical, radial array and extend in reference planes parallel to the longitudinal axis of the assembly 10. A groove is located between each adjacent pair of ribs 32. The grooves function as an array of capillaries for controlled containment and delivery of the composition.

Figure 3A:
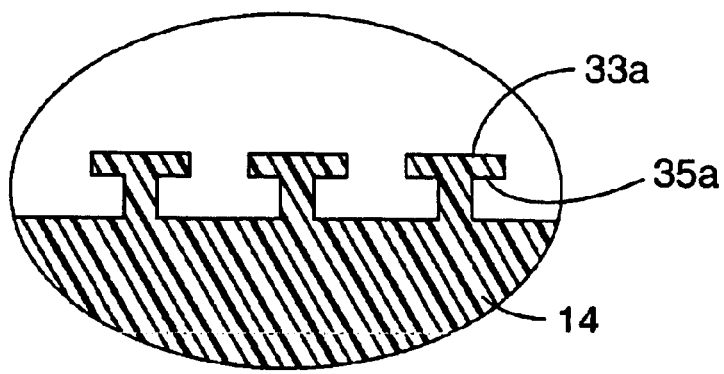
FIGS. 3a–3e are enlarged side cross-sectional views of a portion of the assembly depicted in FIG. 3 according to an optional embodiments of the invention.
Figure 3B:
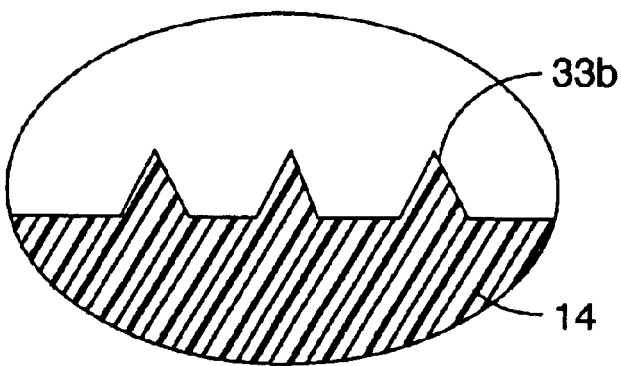
Figure 3C:
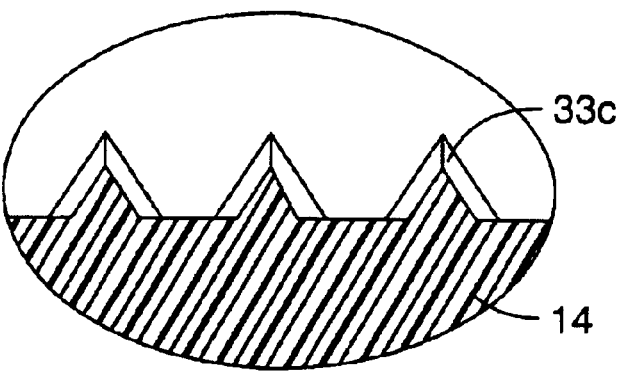
Figure 3D:
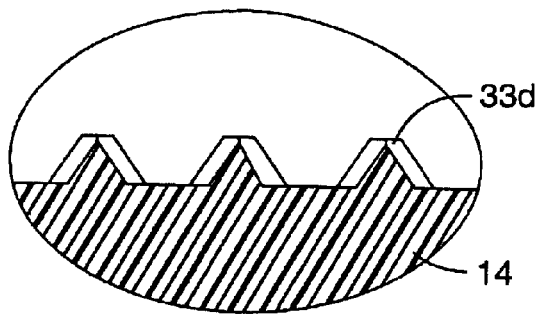
Figure 3E:
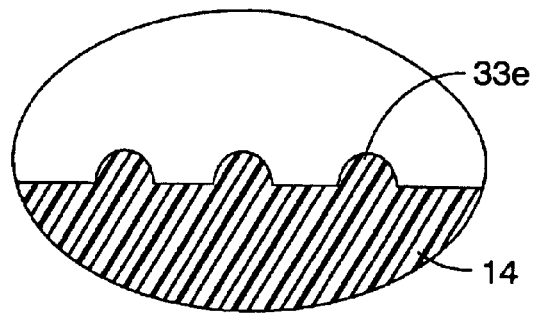

A number of other suitable geometries for the protrusions are also possible. For example, the protrusions may include a series of circular ribs that extend in reference planes perpendicular to the longitudinal axis of the assembly 10. Alternatively, the protrusions may comprise a series of pegs, cones (such as cones 33b in FIG. 3b), pyramids (such as pyramids 33c in FIG. 3c), truncated pyramids (such as truncated pyramids 33d in FIG. 3d), rounded bumps (such as bumps 33e in FIG. 3e) or other types of spaced apart projections. The protrusions may also optionally include undercut regions, such as may be provided by mushroom-shaped projections or nail head-shaped pegs. Examples of nail head-shaped pegs 33a having undercut regions 35a for the container 14 are shown in FIG. 3a. The surface 30 may also include any combination of the foregoing. However, the ribs 32 as described above are substantially less difficult to manufacture.

Optionally, the roughened surface 30 is a microstructured surface, similar to the types described in U.S. Pat. No. 5,514,120 and WO99/65704 (both of which are incorporated by reference herein).

In use, the assembly 10 is grasped by the user, preferably with one hand on the container 14 and the other hand on a collar 34 that surrounds the shaft 20 next to the container 14. Four radially-extending wings 36 facilitate gripping the container 14. Next, the applicator 12 and the container 14 are moved relative to each other in an arc such that the longitudinal axis of the applicator 12 rearwardly of the flexible portion 24 moves from a position collinear with the longitudinal axis of the container 14 to an orientation at a non-zero angle relative to the longitudinal axis of the container 14. During this bending movement, the line of weakness 28 fractures along all or at least a portion of its circumscribing length. Such bending motion of the container 14 relative to the applicator 12 will also cause the flexible portion 24 to bend.

The container 14 is then moved away from the handle 18 in a direction along the length of the applicator 12 in order to uncover the tip 22. The flexible portion 24, having moved past its yield point during the bending motion as the container 14 is removed, remains in its deformed, bent orientation as illustrated in FIG. 3 after the container 14 is separated from the applicator 12. If the user is not satisfied with the resultant angular orientation, the container 14 can be temporarily replaced onto the applicator 12 for additional bending. As a result, the tip 22 and the composition on the tip 22 need not contact the user's fingers or any other structure during any additional bending movements.

FIGS. 1 and 2 illustrate the assembly 10 as it initially appears while FIG. 3 depicts the assembly 10 after the container 14 has been detached from the applicator 12 and the shaft 20 has been bent in the region of the flexible portion 24. As can be appreciated, bending of the applicator 12 can be carried out simultaneously with detachment and removal of the container 14. Such construction represents a time savings for the user, in that a separate step of bending the applicator 12 after removal of the container 14 is not normally required.

Additionally, bending of the applicator 12 simultaneously with detachment of the container 14 enables the applicator 12 to be bent to any desired angular orientation without fear of contamination of the tip 22, the tapered portion 26, the flexible portion 24 or the composition on the tip 22. Such construction avoids the need to grasp the uncovered tip 22 with one hand for bending the flexible portion 24, or the need to press the tip 22 against some other surface for bending the flexible portion 24. The tip 22 and the composition remain safely covered by the container 14 until the desired angular orientation is attained.

The ribs 32 and the adjacent grooves shown in FIG. 4 serve to retain the composition in a location adjacent the tip 22 before such time as the assembly 10 is opened. As a consequence, the tip 22 is likely to remain saturated with the composition during storage and before use regardless of orientation of the assembly 10. When the tip 22 is withdrawn from the chamber 16, the applicator 12 is ready for immediate use and the probability is increased that the composition is uniformly distributed along all of the side portions of the tip 22.

Additionally, the protrusions facilitate re-wetting of the tip 22 when desired. For example, if the composition initially retained on the tip 22 is transferred to a work site and the user determines that an additional quantity of the composition is needed, the tip 22 can be replaced in the container 14 and moved into a position of contact with the ribs 32. As the tip 22 moves along the ribs 32, the composition is transferred from the ribs 32 to the tip 22 for effective re-wetting of the latter.

Another advantage of the protrusions is that the composition tends to remain in contact with the roughened surface 30 until such time as it is transferred to the tip 22. The flow of the composition to other areas of the applicator 12 is hindered, such as areas along the flexible portion 24, the tapered portion 26 or the first section of the chamber 16. The protrusions also help to retain the composition in the container 14 if the container 14 is inverted after separation from the applicator 12. Such construction reduces the likelihood that the composition will contact the users fingers or otherwise create a mess that requires cleaning. Moreover, such construction helps ensure that additional composition is available if needed to re-wet the tip 22.

A presently preferred method of making the assembly 10 includes an initial step of injection molding the container 14 and the collar 34 as one integral component, while simultaneously forming the line of weakness 28. A suitable material for the container 14, the collar 34 and the applicator 12 is a filled polypropylene. Optionally, the ribs 32 provided in the inner portion of the container 14 are made by a microstructured manufacturing technique such as described in the references mentioned above.

Next, a quantity of composition is placed in the container 14 in an area in contact with the inner surface 30. To this end, a thin, hollow dispensing probe may be placed in the chamber 16 in an orientation such that an outlet of the probe is next to the ribs 32. The composition is directed through the probe and onto the surface 30 so that other interior surfaces of the container 14 are avoided.

Subsequently, the applicator 12 is placed within the assembly of the container 14 and the collar 34. A suitable applicator 12 is the "Microbrush" brand applicator described above. The applicator 12 is moved into the chamber 16 a distance sufficient to shift the tip 22 to a location adjacent the inner surface 30.

Next, the applicator 12 is bonded to the collar 34. Preferably, the bond includes a fluid seal. Examples of suitable bonding techniques include press fitting, adhesive bonding, ultrasonic bonding, or by any combination of the foregoing. Optionally, a press-fit assembly technique can be carried out in such a manner as to cause frictional heat to be generated for welding the plastic parts together, such as described in U.S. Pat. No. 4,997,500 (which is incorporated by reference herein). The applicator may also be bonded to the collar by a spin-welding technique.

An example of a spin-welding technique is carried out by holding the applicator 12 stationary while the container is rotated rapidly about its longitudinal axis. As the container 14 along with the collar 34 are spun, friction is created between the inner surface of the collar 34 and the outer, adjacent surface of the shaft 20 such that the synthetic resinous material of the shaft 20 and the collar 34 softens. Once a sufficient amount of friction is created, rotational movement of the container 14 and collar 34 is halted and the plastic is allowed to cool. Once the plastic is cooled, a secure, spin-welded joint is established between the collar 34 and underlying portions of the shaft 20.

A variety of alternative constructions are also possible. For example, the collar described above could be longer such that the shaft of the applicator is surrounded along its entire length. Also, both the container and the applicator may have shapes other than those shown in the drawings. For example, the container could have a flat, rectangular overall shape, with a lower injection molded component that is relatively stiff and an upper cover made of a flexible film that is peeled away from the lower component in order to expose the applicator.

Furthermore, the composition in the applicator may be made of two or more components that are not mixed until immediately prior to use. As an example, one component may be initially separated from the other component by a frangible connection. Optionally, the applicator may be used to fracture the frangible connection. Preferably, mixing of the two components occurs across the roughened surface. Optionally, one of the components is a powder.

A number of other variations are also possible. Accordingly, the invention should not be deemed limited to the specific constructions and methods described above, but instead only by a fair scope of the claims that follow along with their equivalents.

What is claimed is:

1. A method of dispensing a composition comprising:
   providing an assembly that includes a container and an applicator, wherein the container has an inner surface with a plurality of protrusions;
   applying a composition to the protrusions, wherein the act of applying a composition to the protrusions includes the act of applying a dental composition to the protrusions;
   moving a tip of the applicator across the protrusions while contacting the composition on the protrusions; and
   withdrawing the tip from the container.

2. A method of dispensing a composition according to claim 1 and including the act of fracturing a frangible connection between the applicator and the container.

3. A method of dispensing a composition according to claim 1 wherein the act of providing an assembly that includes a container and an applicator includes the act of injection molding the container.

4. A method of dispensing a composition according to claim 1 and including the act of returning the tip to a position inside the container for additional contact with the composition.

5. A method of dispensing a composition according to claim 1 wherein the act of providing an assembly that includes a container and an applicator includes the act of establishing a seal between the container and the applicator.

6. A method of dispensing a composition according to claim 1 wherein the act of providing an assembly that includes a container and an applicator includes the act of providing a frangible connection between the container and the applicator.

7. A method of dispensing a composition according to claim 6 and including the act of rupturing the frangible connection between the container and the applicator prior to the act of withdrawing the tip from the container.

8. A method of dispensing a composition comprising:
   providing an assembly that includes a container and an applicator, wherein the container has an inner surface with a plurality of protrusions;
   applying a composition to the protrusions;
   moving a tip of the applicator across the protrusions while contacting the composition on the protrusions;
   withdrawing the tip from the container;
   and including the act of detaching the container from the applicator and the act of bending a shaft of the applicator as the container is detached from the applicator.

9. A method of dispensing a composition according to claim 8 wherein the act of detaching the container from the applicator includes the act of fracturing a frangible connection between the container and the applicator.

10. A method of dispensing a composition according to claim 1 wherein the act of providing an assembly that includes a container having an inner surface with a plurality of protrusions includes the act of providing a series of ribs that extend in a direction generally parallel to a longitudinal axis of the container.

11. A method of dispensing a composition according to claim 1 wherein the act of providing an assembly that includes a container having an inner surface with a plurality of protrusions includes the act of providing protrusions selected from the group of ribs, pegs, cones, pyramids, truncated pyramids and bumps.

12. A method of dispensing a composition according to claim 1 wherein the act of providing an assembly that includes a container having an inner surface with a plurality of protrusions includes the act of providing protrusions that include at least one undercut area.

13. A method of dispensing a composition according to claim 1 wherein the act of providing an assembly that includes a container having an inner surface includes the act of providing an inner surface that surrounds the tip.

14. A method of dispensing a composition according to claim 1 wherein the act of moving a tip of the applicator across the protrusions includes the act of moving a tip having a roughened surface across the protrusions.

15. A method of dispensing a composition according to claim 14 wherein the act of providing a tip having a roughened surface includes the act of providing a tip having a roughened surface selected from the group of fibers, bristles, porous material, microstructured surfaces, fabrics and gauzes.

16. A method of dispensing a composition according to claim 1 wherein the act of applying a dental composition to the protrusions includes the act of providing a dental composition selected from the group of a dental primer, a dental adhesive, a dental etchant or a dental sealant.

17. A method of dispensing a composition according to claim 1 wherein the act of providing an assembly that includes a container and an applicator includes the act of providing an applicator that has a handle that protrudes from the container when the applicator is received in the container.

\* \* \* \* \*